United States Patent

Masterson et al.

[11] Patent Number: 6,043,895
[45] Date of Patent: Mar. 28, 2000

[54] RADIATION PROBE WITH FLEXIBLE SLEEVE

[75] Inventors: Brian K. Masterson, Placerville; Calvin E. Reynolds, Cameron Park; Terry R. Todd, Placerville, all of Calif.

[73] Assignee: UOP LLC, Des Plaines, Ill.

[21] Appl. No.: 09/189,757

[22] Filed: Nov. 10, 1998

[51] Int. Cl.[7] .................................................. G01N 21/01
[52] U.S. Cl. ............................................. 356/436; 385/12
[58] Field of Search ..................... 356/300, 410, 356/436, 440; 385/12, 113; 250/341.2

[56] References Cited

U.S. PATENT DOCUMENTS

| | | | |
|---|---|---|---|
| 4,192,614 | 3/1980 | deMey, II et al. | 356/410 |
| 4,786,171 | 11/1988 | LeFebre et al. | 356/326 |
| 4,896,940 | 1/1990 | Kathiresan et al. | . |
| 5,078,493 | 1/1992 | Evens et al. | 356/246 |
| 5,140,169 | 8/1992 | Evens et al. | 250/576 |
| 5,140,661 | 8/1992 | Kerek | 385/81 |
| 5,355,423 | 10/1994 | Phillips | 385/12 |
| 5,526,112 | 6/1996 | Sahagen | 356/436 |

*Primary Examiner*—F. L. Evans
*Attorney, Agent, or Firm*—Thomas K. McBride; John G. Tolomei

[57] ABSTRACT

A probe for fiber optic spectroscopy, having a radiation transparent window for the emission of radiation and an optical fiber that extends through the interior of a hollow housing, surrounds the fiber with a cushioning sleeve to provide an optical cable that preserves optical fiber connections and dampen vibration of the optical cable. The sleeve provides a structure around the optical fiber that is more compressible than the optical fiber and has a significantly greater mass than the optical fiber. Excess cable length may be provided along its path through the housing to impinge the cable against the interior walls of the housing and thereby dampen vibration by providing additional node points through contact of the sleeve with the housing wall. Helical twisting of the cable along its path through the housing further stabilizes the shape of the fiber optic cable within the housing and maintains a regular spacing of contact points with the housing. Regular spacing of node points consistently controls vibration dampening by contact between the housing wall and the cable.

22 Claims, 3 Drawing Sheets

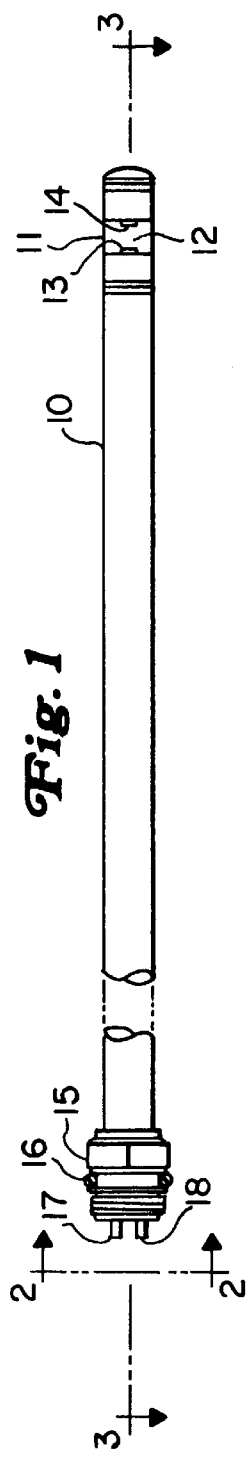
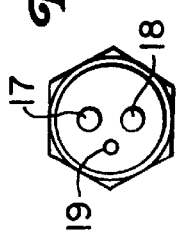
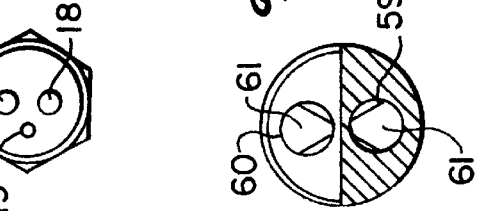
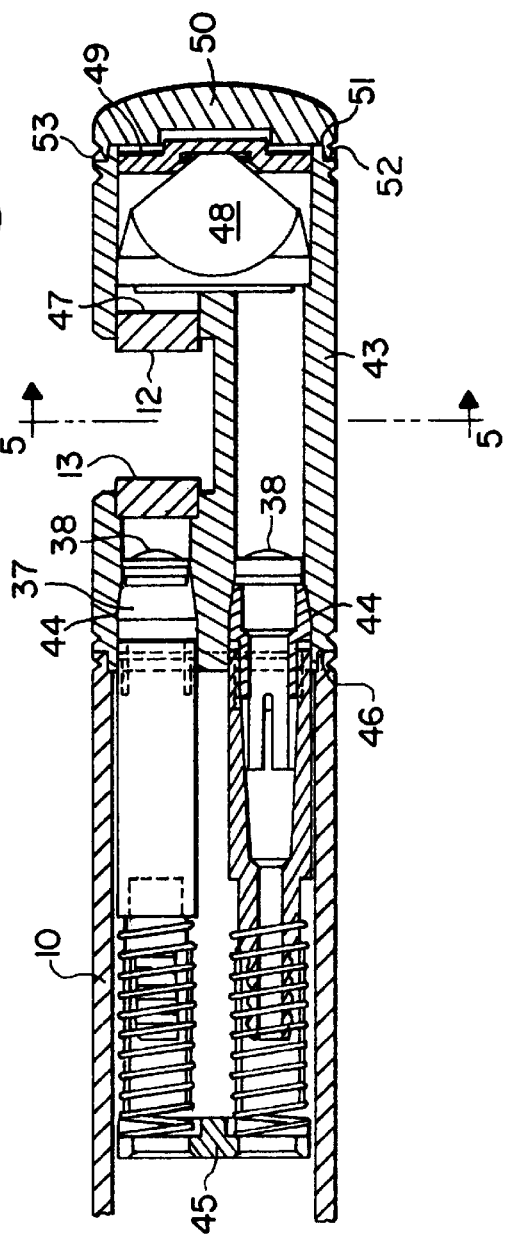
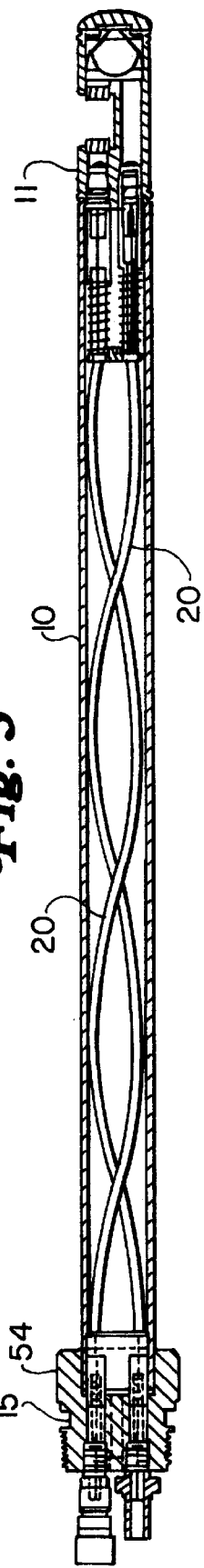

RADIATION PROBE WITH FLEXIBLE SLEEVE

FIELD OF THE INVENTION

This invention generally relates to spectrophotometric detectors for measuring radiation from a radiation source via a probe. More specifically, this invention relates to the arrangement of probes that are inserted into a sample path and through which the radiation passes by means of fiber optic cables.

BACKGROUND OF THE INVENTION

The use of spectrophotometry has been applied to a wide range of materials to determine properties by measuring the adsorbance of radiation through gas, liquid, or solid samples. In the most common arrangements, radiation passes from an emitter, through an entrance window, a sample and an exit window on its way to a detector. Specifically, fluid samples may be withdrawn for flow through a dedicated sample cell or a probe may introduce one or both of the windows into a sample stream or reservoir. The probes and flow cells typically include a lens to collimate or focus radiation through the window in a desired pattern. The direction of radiation transmission and detection may be parallel to the flow of a sample through the cell or the radiation and sample may have a crossflow arrangement. Parallel and cross-flow arrangements for cells are disclosed in U.S. Pat. Nos. 4,192,614 and 5,078,493; the contents of which are hereby incorporated by reference. Fiber optic cables transmit radiation from a radiation source to the sample point and from the sample point to a radiation detector. The operation of a spectrophotometer apparatus and its method of use are fully disclosed in U.S. Pat. No. 4,786,171; the contents of which are hereby incorporated by reference. U.S. Pat. No. 5,140,661 shows details of fiber optic cable and connectors for use therewith.

Probes typically comprise an opposing pair of radiation transparent windows that allow radiation to pass from a radiation emitter, through the sample and on to a detector. The insertion of these probes into process streams exposes them to temperature and pressure extremes as well as to other environmental conditions such as humidity, vibration, and corrosively that are associated with the particular process that uses them. Thermal expansion of different probe components poses a substantial problem. The probe bodies are typically made of stainless steel or other higher metallurgy which has a coefficient of expansion on the order of 10 times higher than coefficient of expansion of the silica material that forms most optical fibers. Probe arrangements routinely insert optical fibers, with or without sheathing, into stainless steel tubes which extend into a probe body. At probe operating temperatures of about 300° C., the differential expansion exerts tension on the optical fibers and imposes significant stress on the fiber bonds at opposite ends of the tubes. The typical small internal diameter of the tubes that contain the fiber optic cables, on the order of $3/16^{th}$ of an inch or less, severely restricts the packing of excess fiber into the tube to accommodate the differential expansion between the fiber and the tube. In most cases the packing of excess fiber only amounts to a few thousandths of an inch. Failure of these bonds would result in loss of optical throughput or efficiency, possible appearance of spectral or temporal etalon fringes (Edser-Butler fringes), fractures in the fiber, and excess sensitivity to vibration.

In addition to the direct stresses imposed by thermal expansion, taut fibers vibrate at much higher frequency than loose fibers, often producing frequencies and amplitudes that interfere with the radiation detection and sometimes cause fiber failure. Dampening of the taut fibers by the use of filler material within the tubes often fails to provide an adequate solution due to deterioration of the filler material at high operating temperatures.

It is known in the prior art to use fiberglass sleeving to protect fiber optic cables from thermally induced degradation at high temperature. U.S. Pat. No. 4,896,940 teaches the covering of single optical fibers or fiber optic cables with several protective layers to prevent damage from excessive temperatures and tension on the cables. According to the '940patent, loose fiberglass sleeving may comprise a thermally protective layer. The arrangement of the '940 patent also places Teflon wrapping on the outside of the protective layer that covers the optical fiber. In this arrangement, a protective layer separates the Teflon wrapping from the optical fiber.

Accordingly, there is need for a probe with improved capacity to withstand differential expansion of its components.

There is also need for a probe that has improved resistance to damage imposed by vibration of the optical fiber within the probe and induced spectral or temporal noise resulting from vibration.

Accordingly, it is an object of this invention to provide a probe having an increased ability to accommodate differential thermal expansion between the materials of probe construction.

It is a further object of this invention to provide a probe that will minimize or eliminate damage from the vibration of optical fibers and spectral or temporal noise associated with vibration of optical fibers within the probe.

BRIEF DESCRIPTION OF THE INVENTION

This invention encases the optical fiber in a cushioning sleeve that eliminates rigid tubes from a probe arrangement. The cable combination of the sleeve and fiber occupies the interior of the probe in a manner that dampens vibration and in a manner that accommodates relative differential expansion between the optical fiber and the probe body. The cushioning sleeve permits the furnishing of slack optical cable in the probe body. The additional optical cable permits freedom for expansion or contraction of the probe body without imposing significant stresses on the optical cable and its connections within or about the probe. Excess optical cable length allows stuffing and twisting of the cable within a hollow housing defining the probe body. Preferably, the packing of additional optical cable length imposes a low compressive force on the optical fiber that does not significantly change with the temperature and the resulting thermal expansion of the probe components. Usually the length of the cable relative to the distance it extends through housing will be in a ratio of at least 1.03.

Another advantage of providing an excess length of sleeve covered optical cable is the ability to force contact of the optical cable against the interior of the hollow probe housing. Preloading the cable against the interior diameter of the housing establishes additional vibrational nodes at each contact point between the cable and housing interior. Multiplying node points reduces vibration frequency and eliminates damaging vibration cycles and detection noise that masks signals. The relatively soft sleeve material further serves to dampen vibration by dissipating kinetic energy into thermal energy as the interior of the sleeve acts against the cable and the exterior of the sleeve acts against the wall of the housing. Preferably, the relatively soft and compressive sleeve surrounding the optical fiber will have a significantly greater mass than the optical fiber which further serves to reduce natural frequency of the cable and fiber assembly.

The flexible sleeve construction has a number of additional advantages. The connections at the ends of the optical cable are readily bonded through crimping instead of bonding due to the compressible nature of the surrounding sleeve. The arrangement also eliminates the need for filling tubes with dampening materials, such as silicone rubber, that often limits the temperatures at which the probes operate. The probe arrangement is readily constructed from materials that can all withstand sustained temperatures of at least 315° C.

Accordingly, in one embodiment, this invention is a probe for extending inwardly into a sample environment for the transmission of and/or detection of radiation through a sample. The probe includes a hollow extended housing that defines a radiation emission and/or a radiation collection point at an outer end of the housing. The housing retains one or more windows along its length or at its inwardly projecting end. An optical fiber passes through the interior of the housing with its ends fixed with respect to the window and the radiation emission or collection point. The fiber has an alignment in the housing for transmission of radiation from the emission point to the window and/or from the window to the collection point. A flexible sleeve formed from a structure having a greater flexibility than the optical fiber surrounds at least a portion of the optical fiber to provide a fiber and sleeve cable that cushions the optical fiber. The flexible sleeve may comprise a braided fiberglass material. Materials such as fiberglass may impart spectra in the radiation transmitted by the fiber optic cable. It may be necessary to isolate the fiber optic cable from the sleeving material using an intermediate material which imparts no spectra into the transmitted radiation in the spectral region of interest. Teflon tape has been found to be a suitable intermediate layer which imparts no spectral content into the transmitted radiation. The length of the fiber and sleeve arrangement will exceed the distance between the window and its respective transmission or collection point. In addition to its mass, the additional length of the sleeve will provide vibrational dampening of the cable by contact with the housing. Helical winding of the cable within the housing provides a well controlled method of packing additional cable into the housing and maintaining the cable in contact with the housing wall.

In another embodiment, this invention is a transmission cable for analog spectroscopic light level measurements. The cable comprises a central optical fiber for transmitting or receiving a broad wavelength spectrum of light. An intermediate shield surrounds the outside of the optical fiber to minimize or eliminate evanescent wave absorption. A braided sleeve surrounds the shield and fiber. The preferred spectral shield comprises a wrapping of Teflon tape between the optical fiber and a braided sleeve made of woven fiberglass strands.

Additional details and embodiments of the probe and cable are disclosed in the following detailed description of the invention.

BRIEF DESCRIPTION OF THE DRAWINGS

FIG. 1 is a plan view of an optical probe.

FIG. 2 is a view of the back of the probe taken along lines 2—2.

FIG. 3 is a cros section of the probe taken along section 3—3 of FIG. 1.

FIG. 4 is an enlarged view of the sample end of the probe of FIG. 3.

FIG. 5 is a cross-section of the sample end of the probe taken across section 5—5 through the sample area of the probe.

DETAILED DESCRIPTION OF THE INVENTION

Figure 6:
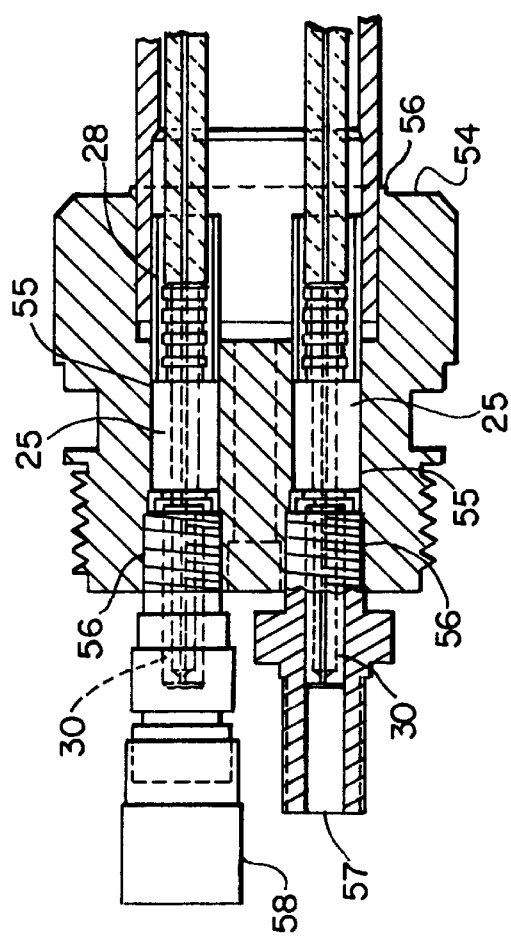
FIG. 6 is an enlarged view of the back of the connector portion of the probe of FIG. 3.

The probe arrangement of this invention is used to deliver or receive radiation for measurement of its absorbance through a fluid or solid sample. In this regard the probe of this invention will contain a fiber optic cable to deliver a radiation source to a window disposed at a sample point. Another fiber optic cable will extend through a probe to return radiation from the sample point through a window to radiation detection apparatus. One probe may contain separate optical fibers for both radiation and emission and detection. Alternately, separate probes may each retain one of the optical fibers that position one of the sending or receiving windows at a sample point. A probe containing a single fiber may also be arranged for the emission and detection of radiation in opposite directions on the same fiber. The details of this invention focus on the probe arrangement and fiber optic cable construction. Additional details of the fiber optic cable and preferred components for the transmission of the radiation source are disclosed in the following detailed description of the preferred embodiment which is not meant to limit the scope of this invention to the particular details disclosed therein.

The core component of this invention consists of a fiber optic cable. The typical fiber optic cable for use in this invention has a glass fiber core, typically of fused silica. The diameter of the core may approach thicknesses of 1 millimeter, but typically, the diameters are in a range of from 200 to 600 micrometers. Preferred optical cores will also include a relatively thin, transparent cladding layer having a different refractive index than the core. A thin coating will usually surround the core and any cladding. The use of a thin polyimide layer, on the order of 10 to 20 micrometers, is a well known coating material. 315° C. is generally the limit of polyimide coatings. Higher temperature applications may be performed using metallic coatings and high temperature epoxies for the connections. For purposes of this description, the core, cladding, and any coating are referred to collectively as the optical fiber.

It is essential to this invention that the fiber optic cable include a cushioning sleeve that surrounds the optical fiber. The sleeve may consist of any material that can fit snugly and flexibly around the optical fiber and will provide a layer having a relative greater compressability than the fiber in order to provide cushioning between the fiber any other surface that contacts the outside of the sleeve. The sleeve should have thermal stability that will enable it to retain its structure and cushioning effect at temperatures greater than 300° C. and, in particular, greater than 315° C.

Woven materials have been found to be particularly suitable for providing the sleeve structure. The strands used to weave the fiber into the sleeve structure may comprise any material that will have the necessary thermal properties. The woven structure, regardless of the hardness of the strands in the weave, will typically provide the necessary compressiblity for cushioning the optical fiber. The strands in the woven structure may be made from high strength material such as Kevlar or from relatively cheap material such as fiberglass. The woven structure has the additional advantage of facilitating assembly of the cable structure since the woven sleeve may be obtained with a large diameter relative to the optical cable. The woven sleeve is usually stretched, relative to the fiber, to draw down and collapse it snugly about the outside of the optical fiber. In addition to the thermal and cushioning properties, preferred sleeve materials will be opaque to radiation passing through the optical fibers.

Figure 8:
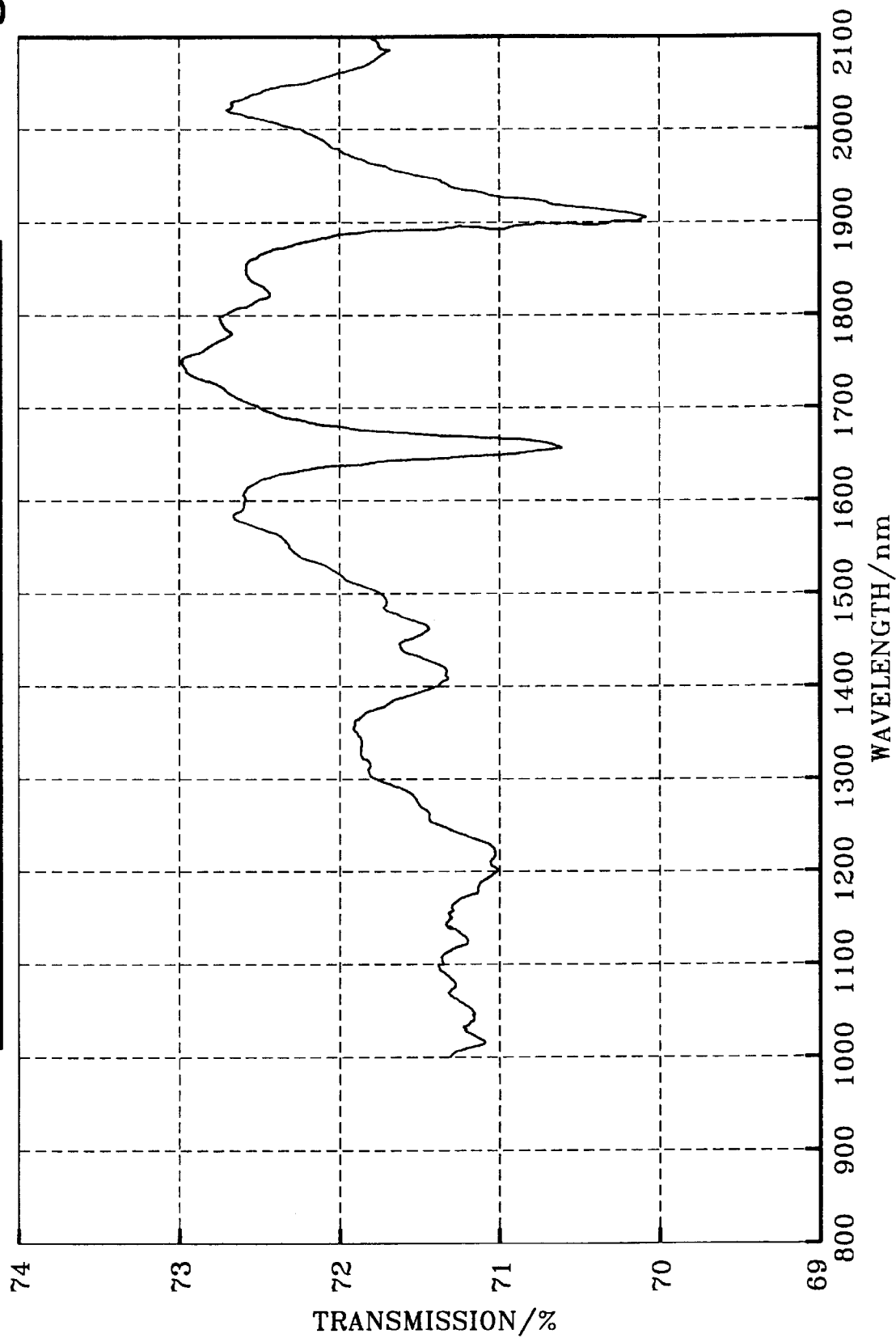
FIG. 8 is a plot of an evanescent wave spectrum.

Fiberglass sleeves are preferred for their low cost and ready availability. Unfortunately, it was unexpectedly discovered that a fiberglass sleeve material exhibited an evanescent wave spectrum. The spectral signature of the fiberglass cable results from evanescent wave adsorption and results in a small fraction of radiation leaking from the core of the optical fiber into the fiberglass across the surface that touches the outer layer of the optical fiber. This evanescent wave interferes with the use of the fiberglass sleeve, particularly in the preferred near infrared range where many of the probes operate. An evanescent wave spectrum of fiberglass was not previously known and such interference was not expected with the transmission of spectral data through the optical fiber with the fiberglass sleeve. FIG. 8 shows the evanescent wave spectrum of the fiberglass sleeve. This spectrum was obtained by first referencing a near infrared spectrometer using a straight 1 m section of optical fiber consisting of an optical cable (core, cladding, and coating in a fiberglass sleeve and then with no Teflon wrap. The optical cable and sleeve were then coiled to a diameter of about 10 cm and the spectrometer was again scanned to produce the difference spectrum shown in FIG. 8. For the reference scan, there was little intimate contact between the optical fiber and the fiber glass. In the second scan, coiling caused intimate contact between the optical cable and the fiberglass sleeve that permitted the evanescent wave to be absorbed by the fiberglass sleeving at or near 1660 nm and 1910 nm. These absorbances will interfere with absorbance from the sample between the windows provided that there is any change in the evanescent couple between the optical cable and fiberglass sleeve. Such coupling is dependent upon the loading stresses on the composite cable and will be temperature dependent. It was found that wrapping the optical cable with a spectrally flat absorbing or scattering material such as Teflon tape eliminates the intimate contact and the introduction of extraneous spectral signatures into the desired spectrum of the sample.

Thus, evanescent wave adsorption for otherwise suitable sleeve materials may be acceptably reduced or eliminated by covering the optical fiber with an opaque barrier. Suitable barriers will have no spectral signature in the desired optical wave length range and will be capable of also withstanding high temperatures of at least 300° C.

A particularly preferred opaque barrier for the near infrared radiation range is Teflon. The use of Teflon as an opaque barrier to prevent optical transmission losses from contact of the fiberglass sleeve with the optical fiber provides a satisfactory solution for the elimination of the evanescent wave spectrum signature on the spectra data obtained from the sleeve and fiber optic cable. Teflon also has the required thermal stability to withstand the temperatures desired for high temperature probe operation. Teflon may be applied to the fiber by any suitable method such as spraying followed by baking. The tape form permits simple helical wrapping of the outside of the fiber before it is inserted into the sleeve. The Teflon tape provides a simple method of providing the opaque barrier for a sleeve such as fiberglass that has an interfering spectral signature in the desired range.

The preferred helical packing arrangement for the optical fiber of this invention provides dual benefits. First, it controls the additional length that accommodates differential expansion between the cable and the housing through which it extends. The additional length of the cable minimizes vibration by keeping the cable slack and avoiding tautness which would induce additional vibration. In addition, it can provide a more continuous contacting of the cable with the wall of the housing to maximize vibration dampening. Obtaining the advantage of vibration dampening also requires intimate contact between the optical fiber and the inside of the sleeve. The rigidity and stiffness of the housing relative to the cable makes each contact point between the housing and the cable function an additional vibration node to shorten the overall unsupported length of the cable and thereby minimize vibration amplitude.

Vibrational dampening also results from the additional mass of sleeve relative to the optical fiber. The additional mass reduces the natural frequency of the cable and minimizes the vibration cycles and amplitude to which the cable is exposed. Small additions of sleeve mass, as little as 10%, can dramatically reduce any vibration at the resonant frequency of the cable. Preferably, the sleeve will have a significantly greater mass than the cable, and the mass ratio of the sleeve to the optical fiber will usually be at least two.

Twisting of the cable into a helical shape also controls the radius of curvature imposed on the optical fiber within the cable. Controlling the radius of curvature of the optical fiber within the housing has important transmission effects on the cable. Short radius bends can fracture the optical fiber and must be avoided in all cases. However, bending imposes transmission losses (called micro bending losses). Micro bend losses occur when a ray being transmitted through the optical core contacts the core cladding interface an angle greater than the critical angle due to the curvature of the fiber and is refracted into the cladding rather than being reflected back into the core. Bending also induces birefringence in fused silica fiber. Birefringence will be exhibited as an inhomogenous change in the indices of refraction of the core and the cladding. The critical angle is a direct function of the indices of refraction of the core and cladding. The critical refraction angle will vary with the material of the optical fiber. For example, quartz has a slightly higher index of refraction than fused silica. Generally, to avoid significant transmission losses from micro bending, this invention seeks to maintain a minimum radius of curvature, anywhere along the cable, of at least 12 cm and, preferably, 15 cm or greater. For most probe sizes, acceptable radii of curvature may be maintained by providing one revolution of the cable in a helical arrangement for about every 15 cm that the cable extends through the housing.

Any housing material may be used for the probe. This invention typically applies to probes that use metallic housings which create the problem of differential expansion between the cable and the probe through which it extends.

All arrangements of the probe use a radiation transparent window to pass the radiation through the sample. The window can be composed of any material having suitable radiation transparency and compatibility with the fluid sample, but it is typically composed of a sapphire, fused silica, or glass. Seals between the window and the housing that holds the window provide the primary seal to maintain separation of a sample fluid from the internal elements of the probe.

DETAILED DESCRIPTION OF THE PREFERRED EMBODIMENT

FIG. 1 generally shows a probe for use in this invention. The probe has an extended housing 10 and a sample end 11 defining a sample space 12 between two optical windows 13 and 14. Opposite sample end 11, the probe has a connector end 15. Connector end 15 may retain an O-ring 16 for sealed communication with a connector body (not shown) that provides an optical connection with connectors 17 and 18. FIG. 2 shows the orientation of connector 17 and 18 in the back of connector 15 along with a pilot hole 19 for injecting materials such as inert gas into the housing.

FIG. 3 shows the internal arrangement of the probe in more detail. Looking then at the hollow interior of sleeve 10, two cables 20 wound in a double helix extend from the connector end 15 to the sample end 11.

Figure 7:
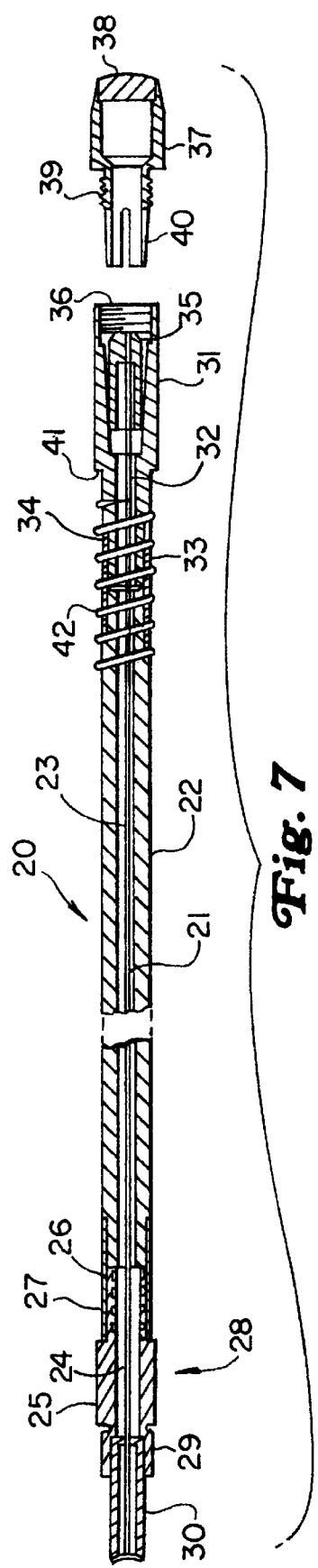
FIG. 7 is an enlarged cross-section of a fiber optic cable for use in the probe of this invention.

FIG. 7 shows the general arrangement of cables 20 in more detail. Cable 20 consists of an optical fiber 21 surrounded by a fiberglass sleeve 22. A winding of Teflon tape 23 provides a radiation barrier between the outside of optical fiber 21 and the inside of fiberglass sleeve 22. The optical fiber has a core diameter of 500 micrometers with a 25 micron cladding around its outside and a 16 micron polyimide coating that together provide the optical fiber with an outside diameter of approximately 582 micrometers. The fiberglass sleeve, before application around the optical fiber, has a nominal $\frac{1}{8}$ inch OD and $\frac{1}{16}^{th}$ inch ID. Stretching of the fiberglass sleeve shrinks the sleeve diameter down to fit snugly against the Teflon tape windings on the cable. Typically, the sleeve need not fit tightly against the optical fiber cable. It is only pulled taut enough to eliminate any puffy or bulging areas between the fiber and the sleeve.

For accommodation with the connector end of the probe the cable has a connector assembly 28 at one end. A portion of stripped optical cable 24 extends through a connector ferrule 25. A ribbed collar 26 extends from ferrule 25. The braided sleeve extends over the ribbed collar 26 and a crimped sleeve 27 holds the fiberglass sleeve in place. A bore 29 of ferrule 25 receives a fiber sleeve 30 that centers portion 24 of the optical fiber at the end of connector assembly 28.

At the opposite end of the cable the probe has a lens retainer. The lens retainer has a lens holder 37 and a collar 31 that receives a stripped portion 32 of the optical fiber cable 21. A crimping arrangement, similar to that described in assembly 28, has a sleeve 33 that retains the fiberglass sleeve around a ribbed collar 34. A positioning sleeve 35 retains the end of the fiber optic cable portion 32. A threaded end 36 of collar 31 receives lens holder 37 that retains a radiation focusing lens 38. A threaded portion 39 of lens holder 37 retains positioning fingers 40 around positioning sleeve 35 so that radiation from the optical fiber is collimated by lens 38 or to focus radiation from a collimating lens 38 into the optical fiber. Collar 31 has a shoulder 41 that is acted against by a spring 42.

On each side of sample space 12, sapphire windows 13 and 14 emit or receive radiation from lenses 38. The window may extends approximately a $\frac{1}{16}^{th}$ inch or less into sample space 12. The extension of the windows into the sample space aids in preventing any fouling of the window surface. In other arrangements it may be desirable to have the window extend into the sample space by greater distances than $\frac{1}{16}$ of an inch in order to yield smaller path lengths.

The functioning of spring 42 in relationship to lens holder 37 is better understood by reference to FIG. 4. FIG. 4 shows a sample body 43 having a pair of conical recesses 44 for receiving a pair of lens holders 37. Springs 42 force the lens holders 37 into alignment in sample body 43 by interaction between the conical surface on the lens holder and the conical recess 44 in the sample body 43. Springs 42 act against a spring retainer 45 that receives the ends of spring 42 and that is fixed with respect to sample body 43. The springs are retained in compression because the distance from the lens holder 37 to the spring retainer 45 is less than the free length of the spring.

Sample body 43 may be attached to housing 10 by any means. Brazing or, preferably, welding usually retains sample body 43 in contact with housing 10 at a seam 46.

Proper alignment of lenses 38 is essential to the proper functioning of the probe and to the emission and collection of radiation to and from the windows 12 and 13. One of lenses 38 may emit or receive radiation directly to or from window 13 and across the sample space. A corner cube reflector 48 transmits radiation from or to the back side of lens 12 and through the lower lens 38. As shown by FIG. 5, the corner cube reflector 48 is positioned in a portion of sample body 43 that provides a lower target opening 58 and an upper target opening 60 for transmitting radiation into and out of the frontal surface 71 of corner cube 48. A spacer 49 holds corner cube reflector 48 into place for refractive alignment of radiation to and from the upper and lower lenses. A shoulder 52 receives a groove 51 of an end cap 50 that retains spacer 49 in place. Again, brazing and preferably welding will normally hold end cap 50 in place at the end of sample body 43.

In normal fabrication, the fiber optic cables and the connector assemblies 28 are inserted through the spring retainers 45 as an initial step. The sample end of the probe is then assembled such that the connector ends of the fiber optic cables extend out of the back of housing 10. Assembly is then completed (reference FIGS. 3 and 6) by extending the connector assemblies 28 of the fiber optic cables into connector end 15 and bores 55 of connector body 54. An adhesive bonds ferrules 25 into the bores 55 to provide a hermetic seal between the cable ends and the connector body 54. Rotation of connector body 54 by a desired number of rotations, depending on the length of housing 10, provides the desired degree of twisting of the cables, and hence the accumulation of the appropriate amount of extra fiber cable length within the housing. Once the cables have been twisted to the desired degree, welding or brazing of connector body 54 to housing 10 along seam 56 permanently holds the cables in the desired twisted shape within the housing 10. Connector body 54 may have threaded ends to retain an SMA connector 57, an FA connector 58 or an ST connector (not shown) around sleeve 30.

Contact of the twisted fibers with walls of housing 10 will normally provide sufficient vibration dampening to eliminate noise readings from the probe and damage to the fiber optic cable. It is also possible to provide additional packing, such as beads, within the remaining open volume of housing 10 to further dampen any movement and vibration of the cable 20.

The housing may be made of any material and any size necessary to provide sufficient rigidity for probe placement and operation within the environment into which the probe is inserted. The housing material usually comprises a metallic alloy such as stainless steel or other well known nickel chrome and iron alloys. Normally, the probe housing will have an outside diameter in a range of from $\frac{3}{4}$" to 1" and a wall thickness of about $\frac{1}{16}^{th}$ to $\frac{3}{8}$ of an inch.

Once assembled port 19 may be used to provide an inert gas into the interior of housing 10. A threaded set screw may close off port 19 to provide a final seal for the interior of the probe. The set screw may be coated with a suitable sealing adhesive.

Those skilled in the art can readily appreciate that the flow cell arrangement is susceptible to a variety of variations for which no patent protection is hereby relinquished by the specific description herein as set forth in the following claims.

What is claimed is:

1. A probe for extending inwardly into a sample environment for the emission and/or collection of radiation through a sample, the probe comprises:
    a) a hollow extended housing having an inwardly projecting end;
    b) a radiation emission point and/or a radiation collection point defined at an outer end of the housing;
    c) a window disposed at a sample point located, along the length of, or at the inwardly projecting end of the extended housing;
    d) an optical fiber passing through the interior of the housing, fixed at its ends with respect to the window and to the radiation emission point or collection point, and aligned in the housing for optical transmission of radiation from the emission point to the window and/or from the window to the collection point;
    e) a flexible sleeve formed from a structure having a greater flexibility than the optical fiber and surrounding at least a central portion of the optical fiber to provide a fiber and sleeve cable that cushions the optical fiber; and
    f) a shield, opaque to a selected radiation wave length band, separating the outside of the optical fiber from the inside of the flexible sleeve.

2. The apparatus of claim 1 wherein the window is located proximate to the inwardly projecting end of the housing.

3. The apparatus of claim 1 wherein the probe contains a transmitting window that transmits radiation from the emission point to a collection window along a sending optical fiber and a receiving window that transmits radiation to the collection point along a receiving optical fiber.

4. The apparatus of claim 3 wherein portions of the sending and receiving optical fibers pass through a common section of the housing.

5. The apparatus of claim 1 wherein the flexible sleeve comprises a braided fiberglass material.

6. The apparatus of claim 5 wherein a layer of Teflon separates the outside of the optical fiber from the braided fiberglass material to shield the optical fiber from the spectrum of the fiberglass material.

7. The apparatus of claim 1 wherein the length of the fiber and sleeve cable exceeds the distance between the window and the transmission point or the collection point.

8. The apparatus of claim 7 wherein the ratio of the fiber and sleeve cable length to the distance that the fiber and sleeve cable extends through the housing is at least 1.03.

9. The apparatus of claim 1 wherein a dampening arrangement dampens vibration of the flexible sleeve.

10. The apparatus of claim 9 wherein contact of the sleeve with the inner wall of the housing provides vibration dampening.

11. The apparatus of claim 9 wherein the optical fiber and sleeve cable is helically twisted into contact with the inner wall of the housing between the window and the emission point to provide vibration dampening.

12. The apparatus of claim 11 wherein the relative angular rotation of the fiber and sleeve cable equals about one revolution for every 15 cm that the fiber and sleeve cable extends through the housing.

13. The apparatus of claim 11 wherein the radius of curvature of the fiber and sleeve cable is not less than 12 cm.

14. The apparatus of claim 9 wherein the housing retains two fiber and sleeve cables and the two cables are twisted into a double helix that contacts the wall of the housing.

15. The apparatus of claim 9 wherein the mass ratio of the sleeve to the optical fiber is at least 2.

16. The apparatus of claim 1 wherein the sleeve is formed from a material that will remain dimensionally stable and will not degrade at a temperature of at least 315° C.

17. A probe apparatus for the emission and detection of radiation across a sample, the apparatus comprising:
    a) a hollow extended housing;
    b) an emission window and a collection window arranged in an opposing relationship and separated from each other to define a gap that provides a sample point proximate to a sampling end of the extended housing;
    c) an emission optical fiber extending through the interior of the housing, a spectral shield surrounding the outside of the optical fiber, and a braided fiberglass sleeve surrounding the shield and fiber to provide a first transmission cable;
    d) a collection optical fiber extending through the interior of the housing, a spectral shield surrounding the outside of the collection optical fiber and a braided fiberglass sleeve surrounding the shield and fiber to provide a second transmission cable;
    e) a radiation emission connection defined at a sampling end of the housing that receives a first end of the first transmission cable and biases the emission optical fiber into optical communication with the emission window;
    f) a radiation collection connection defined at the sampling end of the housing that receives a first end of the second transmission cable and biases the collection optical fiber into optical communication with the collection window; and
    g) a pair of end connections joining respective second ends of the transmission cables to an end of the housing opposite the sampling end.

18. The apparatus of claim 17 wherein each radiation emission and radiation collection connection retains a lens between its optical fiber and one of the windows.

19. A transmission cable for analog spectroscopic light level measurements, the cable comprising:
    a central optical fiber for transmitting or receiving a broad wavelength spectrum of light;
    an intermediate spectral shield surrounding the outside of the optical fiber; and,
    a braided sleeve surrounding the shield and fiber.

20. The apparatus of claim 19 wherein the spectral shield comprises a wrapping of Teflon tape.

21. The apparatus of claim 20 wherein the braided sleeve comprises woven fiberglass strands.

22. A probe for extending inwardly into a sample environment for the emission and/or collection of radiation through a sample, the probe comprises:
    a) a hollow extended housing having an inwardly projecting end;
    b) a radiation emission point and/or a radiation collection point defined at an outer end of the housing;
    c) a window disposed at a sample point located, along the length of, or at the inwardly projecting end of the extended housing;

d) an optical fiber passing through the interior of the housing, fixed at its ends with respect to the window and to the radiation emission point or collection point, and aligned in the housing for optical transmission of radiation from the emission point to the window and/or from the window to the collection point; and e) a flexible sleeve formed from a structure having a greater flexibility than the optical fiber and surrounding at least a central portion of the optical fiber to provide a fiber and sleeve cable that cushions the optical fiber wherein the optical fiber and sleeve cable is helically twisted into contact with the inner wall of the housing between the window and emission point or collection point to dampen vibration of the flexible sleeve.

* * * * *